US011346690B2

(12) United States Patent
Cardenas et al.

(10) Patent No.: US 11,346,690 B2
(45) Date of Patent: May 31, 2022

(54) DEVICE WITH WATER-ACTIVATED, AUTOMATIC DISCONNECT

(71) Applicant: Boston Engineering Corporation, Waltham, MA (US)

(72) Inventors: Robert Lee Cardenas, Framingham, MA (US); Michael Conry, Beverly, MA (US); Michael Rufo, Hanover, MA (US)

(73) Assignee: Boston Engineering Corporation, Waltham, MA (US)

( * ) Notice: Subject to any disclaimer, the term of this patent is extended or adjusted under 35 U.S.C. 154(b) by 92 days.

(21) Appl. No.: 16/854,533

(22) Filed: Apr. 21, 2020

(65) Prior Publication Data
US 2021/0214049 A1  Jul. 15, 2021

Related U.S. Application Data

(60) Provisional application No. 62/959,513, filed on Jan. 10, 2020.

(51) Int. Cl.
*G01D 11/24* (2006.01)
*B63B 22/00* (2006.01)
*B63B 22/08* (2006.01)
*G01D 21/02* (2006.01)
*G06F 8/61* (2018.01)
*B63C 7/26* (2006.01)

(52) U.S. Cl.
CPC .......... *G01D 11/245* (2013.01); *B63B 22/003* (2013.01); *B63B 22/08* (2013.01); *G01D 21/02* (2013.01); *G06F 8/61* (2013.01); *B63B 2022/006* (2013.01); *B63C 7/26* (2013.01)

(58) Field of Classification Search
CPC .... G01D 11/245; G01D 21/02; B63B 22/003; B63B 22/08; B63B 2022/006; G06F 8/61; B63C 7/26; G01N 33/1886; G01N 2201/0218

See application file for complete search history.

(56) References Cited

U.S. PATENT DOCUMENTS

| | | | |
|---|---|---|---|
| 3,906,565 A | 9/1975 | Dorrance et al. | |
| 3,910,457 A * | 10/1975 | Sutliff | B64D 17/38 222/5 |
| 5,209,112 A * | 5/1993 | McCoy | B63B 22/003 73/170.01 |
| 6,772,705 B2 | 8/2004 | Leonard et al. | |
| 6,807,856 B1 | 10/2004 | Webb | |

(Continued)

FOREIGN PATENT DOCUMENTS

| | | |
|---|---|---|
| RU | 2609849 | 2/2017 |
| WO | 2012013962 | 2/2012 |
| WO | 2018067738 | 4/2018 |

*Primary Examiner* — Anthony D Wiest
(74) *Attorney, Agent, or Firm* — BainwoodHuang

(57) ABSTRACT

A technique for managing an attachment between first and second portions of a device. The technique includes a retaining component having a first state in which the retaining component maintains the attachment between the first and second portions by virtue of a rigid characteristic and a second state in which the retaining component loses the rigid characteristic and no longer maintains the attachment. The retaining component transitions from the first state to the second state upon exposure to liquid water.

19 Claims, 9 Drawing Sheets

(56) References Cited

U.S. PATENT DOCUMENTS

| | | |
|---|---|---|
| 8,397,658 B1 | 3/2013 | Imlach et al. |
| 9,709,396 B2 * | 7/2017 | Chedrawy ............. B63B 22/003 |
| 10,638,742 B1 * | 5/2020 | Barnett ................ A01K 97/125 |
| 10,994,818 B2 * | 5/2021 | Hernandez ................ B63C 9/24 |
| 2014/0047682 A1 | 2/2014 | Blackman et al. |
| 2018/0162501 A1 | 6/2018 | Peterson et al. |

* cited by examiner

DEVICE WITH WATER-ACTIVATED, AUTOMATIC DISCONNECT

CROSS-REFERENCE(S) TO RELATED APPLICATION(S)

This application claims the benefit of U.S. Provisional Patent Application No. 62/959,513, filed Jan. 10, 2020, the contents and teachings of which are incorporated by reference herein in their entirety.

STATEMENT REGARDING FEDERALLY SPONSORED RESEARCH OR DEVELOPMENT

This invention was made with government support under WC-133R-15-CN-0112 awarded by the National Oceanic and Atmospheric Administration. The government has certain rights in the invention.

BACKGROUND

Hurricanes in the United States cause billions of dollars in damages annually with an average death rate of nearly 20 persons per year. Accurate measurements in and around hurricanes are critical for predicting hurricane intensity, and thus the severity of risks posed to human life and property. Current approaches to measuring hurricane-related factors employ buoys, sondes, and dropsondes. Buoys are floating devices that make measurements near the surface of a body of water and store collected data, which may be retrieved directly by visiting the buoys or by receiving the data over a wireless link. Sondes are devices that operate within a body of water and collect data as they descend. Relevant data may include conductivity, temperature, and depth, for example. Dropsondes are sondes adapted for deployment from an aircraft. A dropsonde can measure atmospheric conditions while falling through the air. After splashdown, a dropsonde can measure water conditions as it sinks through the water. Sondes and dropsondes may log their data while operating under water and transmit the logged data upon resurfacing. Some sondes and dropsondes may perform "profiling," i.e., controllably rising and sinking to various depths and measuring water columns at different locations.

Dropsondes typically deploy parachutes that enable them to fall through the air at controlled speeds and typically jettison their parachutes upon splashdown. For example, a dropsonde may include a sensor that detects sudden deceleration or contact with water and an actuator that detaches the parachute upon such detection.

SUMMARY

Unfortunately, prior disconnect mechanisms for dropsondes and other devices can be expensive and complex. Actuators consume power and valuable space; they also increase weight. Further, the types of devices described above typically operate in wet, saline environments, which can pose short-circuit risks to electronically controlled actuators.

In contrast with prior approaches, an improved technique for managing an attachment between first and second portions of a device includes a retaining component having a first state in which the retaining component maintains the attachment by virtue of a rigid characteristic and a second state in which the retaining component loses the rigid characteristic and no longer maintains the attachment. The retaining component transitions from the first state to the second state upon exposure to liquid water. Advantageously, the improved technique requires no power, sensor, or control circuitry and operates reliably in salt-water environments.

Certain embodiments are directed to an apparatus. The apparatus includes a first portion, a second portion, and a retaining component. The retaining component has a first state and a second state. In the first state, the retaining component is configured to have a rigid characteristic and to hold the first portion to the second portion. In the second state upon exposure to liquid water, the retaining component is configured to lose its rigid characteristic and to free the first portion from the second portion.

Other embodiments are directed to a method of managing an attachment between a first portion and a second portion of a device. The method includes providing a retaining component having a first state and a second state, the retaining component configured in the first state to have a rigid characteristic and to hold the first portion to the second portion, the retaining component configured in the second state to lose its rigid characteristic upon exposure to liquid water. With the retaining component in the first state, the method further includes the device becoming at least partially submerged in water. The method further includes the device allowing water to pass to the retaining component, the retaining component thereupon transitioning from the first state to the second state and freeing the first portion from the second portion.

The foregoing summary is presented for illustrative purposes to assist the reader in readily grasping example features presented herein; however, this summary is not intended to set forth required elements or to limit embodiments hereof in any way. One should appreciate that the above-described features can be combined in any manner that makes technological sense, and that all such combinations are intended to be disclosed herein, regardless of whether such combinations are identified explicitly or not.

BRIEF DESCRIPTION OF THE SEVERAL VIEWS OF THE DRAWINGS

The foregoing and other features and advantages will be apparent from the following description of particular embodiments, as illustrated in the accompanying drawings, in which like reference characters refer to the same or similar parts throughout the different views. The drawings are not necessarily to scale, emphasis instead being placed upon illustrating the principles of various embodiments.

DETAILED DESCRIPTION

Embodiments of the disclosed technique will now be described. One should appreciate that such embodiments are provided by way of example to illustrate certain features and principles but are not intended to be limiting.

A technique for managing an attachment between first and second portions of a device includes a retaining component having a first state in which the retaining component maintains the attachment by virtue of a rigid characteristic of the retaining component and a second state in which the retaining component loses the rigid characteristic and no longer maintains the attachment. The retaining component transitions from the first state to the second state upon exposure to liquid water.

Figure 1:
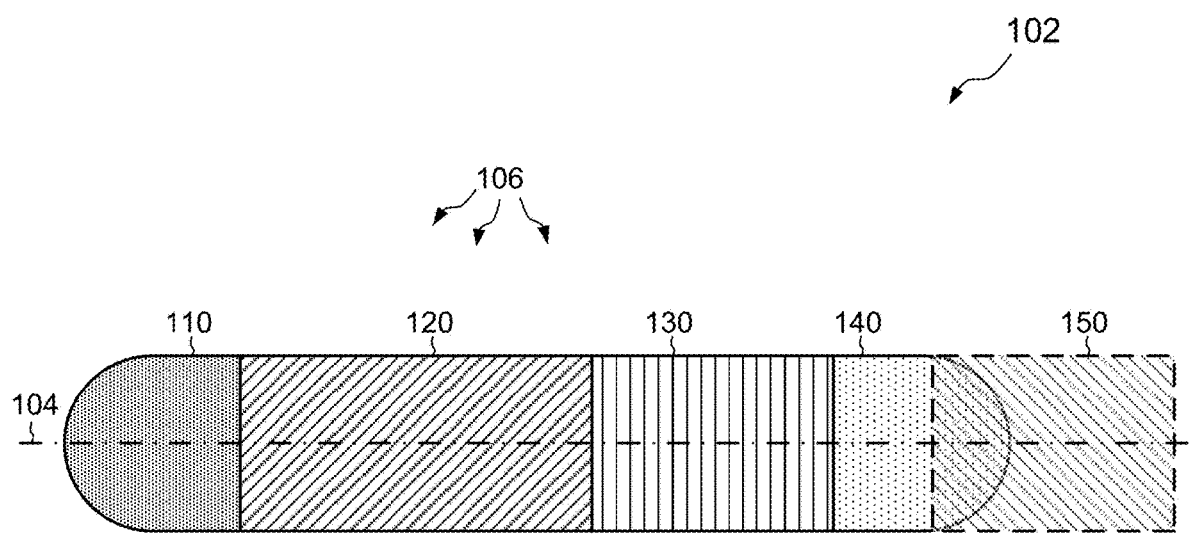
FIG. 1 is a front plan view of an example device in accordance with certain embodiments.

FIG. 1 shows an example device 102 with which embodiments of the improved technique can be practiced. Here, multiple modules 106 are arranged end-to-end along an axis 104 of the device 102. The depicted modules 106 include a nose module 110, a variable buoyancy module 120, an electronics module 130, a communications module 140, and a parachute module 150. Other embodiments may include a greater or fewer number of modules 106, and such modules may be of different types and/or capabilities from those shown. The depicted example is merely illustrative.

Figure 2:
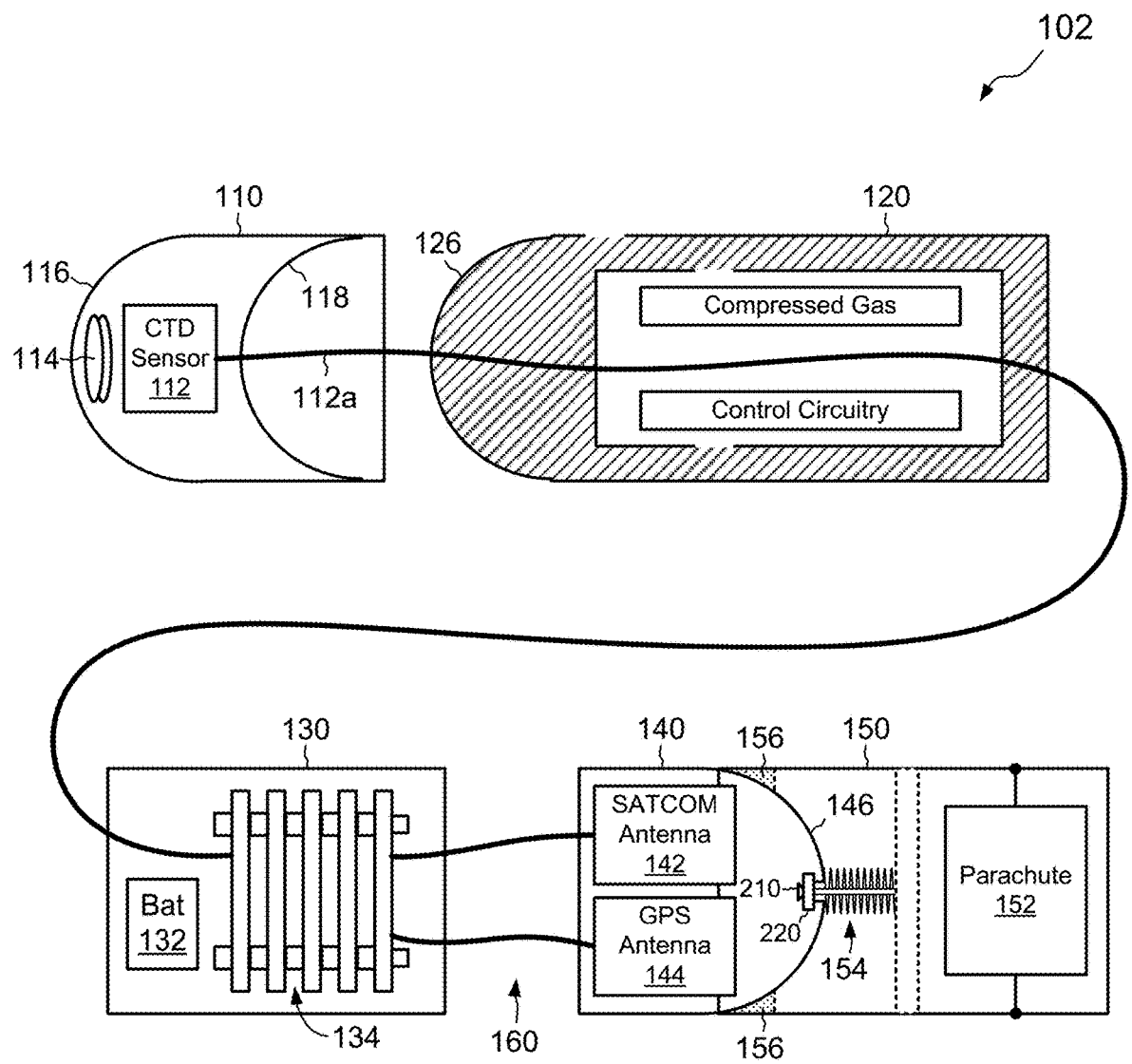
FIG. 2 is a partially exploded view of the device of FIG. 1.

FIG. 2 shows the device 102 in additional detail. Here, nose module 110 is seen to include environmental sensors, such as a CTD (conductivity, temperature, and depth) sensor 112, and ballast (e.g., weights) 114. The ballast 114 assists in keeping the nose module 110 pointing down and the device 102 vertical when the device 102 is submerged in water. Nose module 110 has a convex outer surface 116, which may be hemispherically shaped, for example, to enable the device 102 to descend smoothly under water. In some examples, nose module 110 has a concave inner surface 118 adapted for receiving a convex outer surface 126 of variable buoyancy module 120.

Variable buoyancy module 120 is configured to vary its own buoyancy, and hence the buoyancy of the overall device 102, in response to electronic control. To this end, variable buoyancy module 120 enables the device 102 to controllably rise and fall within a water column.

Electronics module 130 is connected to the variable buoyancy module 120 and includes, for example, a power source such as a battery 132 and an electronics assembly 134. As shown, the electronics assembly 134 is electrically connected to the CTD sensor 112 (and any other environmental sensors in the nose module 110), e.g., via a cable that passes through the variable buoyancy module 120. In some examples, the electronics assembly 134 includes a microcontroller, microprocessor, or the like, as well as associated memory. It may further include an IMU (inertial measurement unit) and electronics for supporting GPS, SATCOM, and/or RF communications, such as interfaces to antennas provided in the communications module 140. In some examples, the power source may be provided in some other module, such as in the variable buoyancy module 120 or in a separate module (e.g., a battery module).

In the example shown, communications module 140 includes a satellite communications (SATCOM) antenna 142 and a GPS (Global Positioning System) antenna 144, which may be electrically connected to the circuit assembly 134 via cables 160. In some examples, one or more RF (Radio Frequency) antennas may be provided, to support RF communication. Communications module 140 may preferably have a convex outer surface 146, e.g., for facilitating upward movement of the device 102 through water. The convex outer surface 146 is preferably made of a non-conductive material, such as poly-vinyl chloride (PVC), to allow electromagnetic signals to readily pass therethrough. The convex outer surface 146 is adapted to mate with a partially-concave inner surface 156 in the parachute module. In some examples, the communications module 140 may include an extendible mast (FIG. 8B) with antennas disposed at a remote end and/or along a length thereof. The extendable mast may serve to raise antennas away from the water surface to improve signal strength.

Parachute module 150 preferably has a detachable connection to communications module 140. As will be described more fully below, a fastener 210 in the communications module 140 attaches to the parachute module 150 and abuts a retaining component 220 that holds the parachute module 150 in place. Spring 154 applies a biasing outward force. The retaining component 220 is configured to soften or dissolve upon contact with liquid water, allowing the spring 154 to pull the fastener 210 through the retaining component 220 and out of the communications module 140, and thus to separate the parachute module 150 from the communications module 140.

Figure 3:
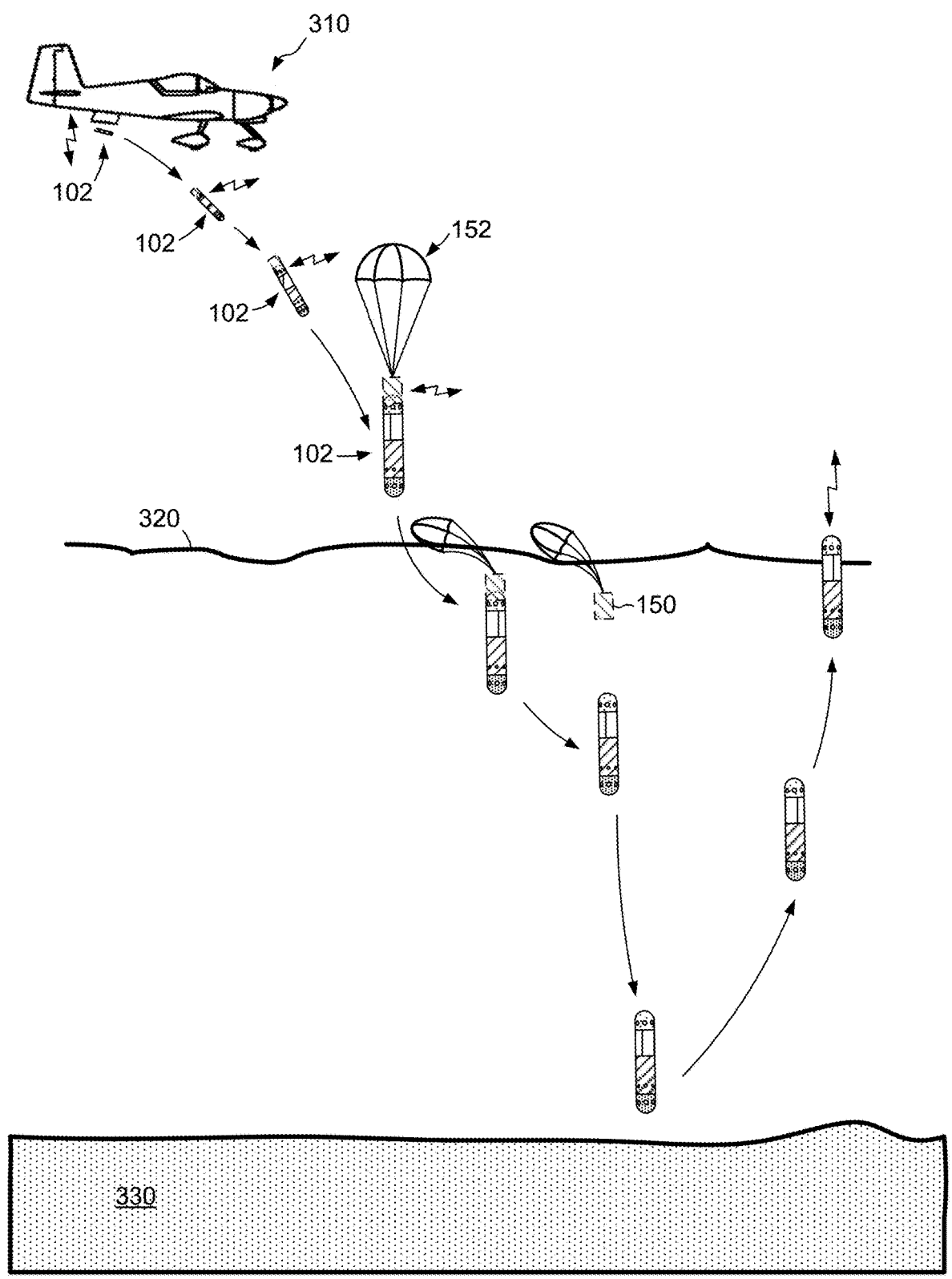
FIG. 3 is a diagram showing an example mission deployment of a device of the kind shown in FIG. 1.

FIG. 3 shows an example deployment of a device 102 for making measurements in an aqueous environment. As shown, an airplane or other aircraft 310 drops or otherwise ejects a device 102, which begins falling through the air. Parachute 152 opens, and device 102 begins a slowed descent, falling nose-first, i.e., with nose module 110 pointing down. Depending on application, the device 102 may monitor environmental factors of the air, such as temperature, pressure, humidity, particulate matter, and so forth, as it descends to through the atmosphere. Device 102 may also monitor its own location and altitude, e.g., using GPS. The device 102 may log the results and/or transmit the results, e.g., via SATCOM, to a remote receiver (not shown).

The device 102 eventually splashes down, striking the surface 320 of a body of water. In some examples, the device 102 collects surface data at this time. After exposure to liquid water, the parachute module 150 automatically detaches from the device 102. The device 102 then begins to descend toward the floor 330 of the body of water, leaving the parachute module 150 behind. The device 102 continues to log data as it goes. For example, device 102 may repeatedly measure conductivity, temperature, and depth. Depending on the mission, the device 102 may perform profiling, e.g., by action of the variable buoyancy module 120, alternately ascending and descending and making measurements of different water columns. Once measurements have been made, the device 102 ascends to the surface 320, whereupon the device 102 transmits the contents of its data log wirelessly to a receiver. Alternatively, personnel may retrieve the device 102 and read its data directly.

Figure 4:
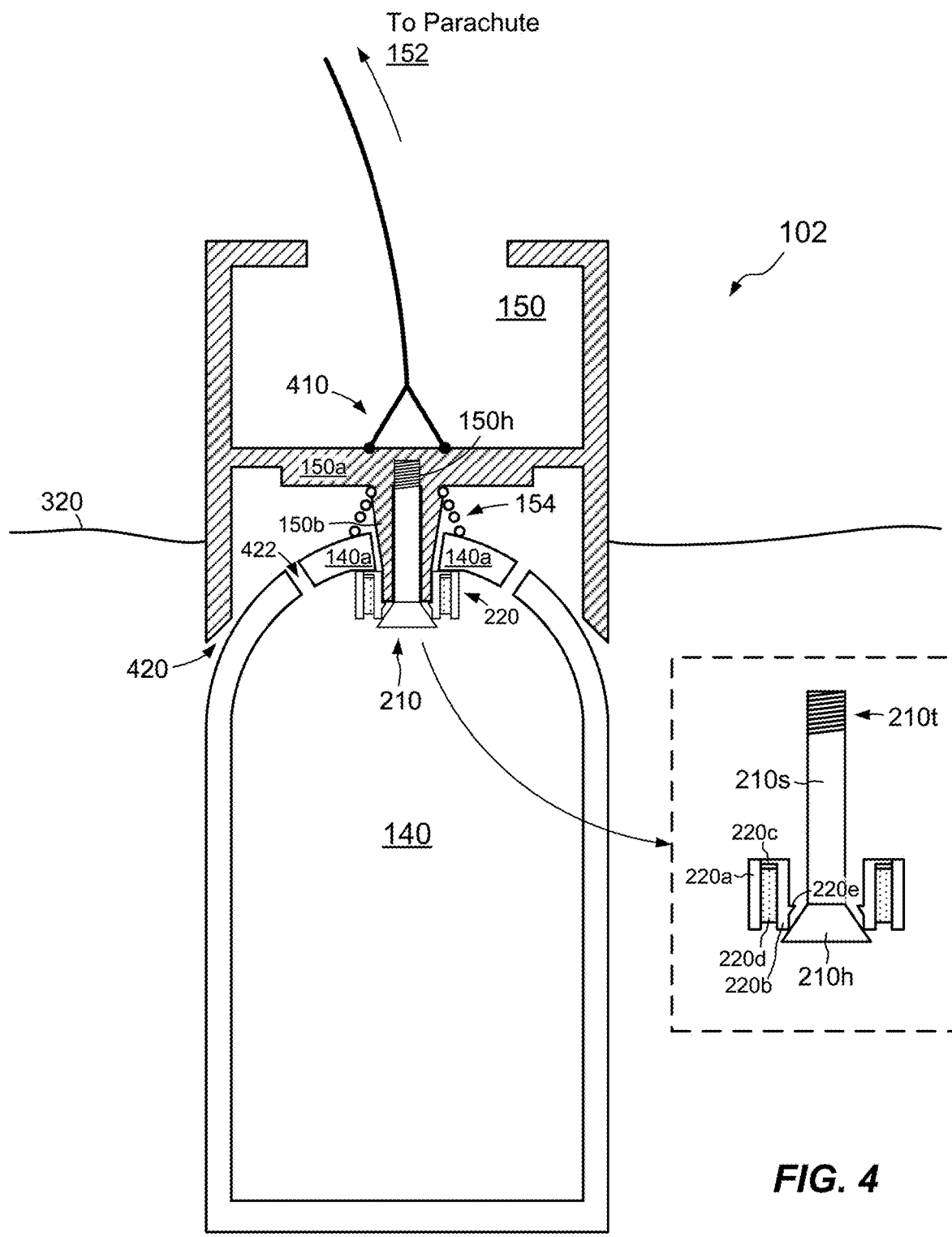
FIG. 4 is a cross-sectional view that shows example parts of the device of FIG. 1, including an example parachute module, communications module, and attachment formed therebetween.

FIG. 4 shows an example attachment between the communications module 140 and the parachute module 150 in greater detail. The additional modules 106 of FIG. 1 are omitted from the figure for simplicity. In the example shown, the parachute 152 has deployed from the parachute module 150 and the device 102 has landed in water. The parachute 152 remains anchored to the parachute module 150 via a parachute anchor 410.

As shown in the main figure and in the magnified partial view to the right, the fastener 210 includes a tapered head 210h, a shaft 210s that extends from the head 210h, and threads 210t formed at a distal end of the shaft 210s. The threads 210t engage with a threaded hole 150h formed within an internal wall 150a of the parachute module 150.

In the example shown, the retaining component 220 has an annular shape and a central hole through which the fastener 210 extends. A shown to the right of the figure, the retaining structure 220 includes a frame having an outer wall 220a, internal fingers 220b, and spokes 220c. Contained within the frame is a bobbin pill 220d. The bobbin pill 220d is composed of a material that is initially rigid and has high compressive strength, even in humid air, but which softens and/or dissolves when exposed to liquid water. Suitable materials for the bobbin pill 220d include microcrystalline cellulose. Bobbins of this type are commercially available from numerous sources, including Halkey-Roberts Corporation of St. Petersburg, Fla.

The internal fingers 220b of the retaining component have internally-projecting steps 220e. In an assembled state, a cone-shaped projection 150b from the wall 150a of the parachute module 150 extends down and rests on the steps 220e. In this condition, the fastener (e.g., a screw or bolt) may be tightened into the threaded hole in the wall 150a until the head 210h of the fastener abuts the internal fingers 220b of the retaining structure 220. In this condition, the spring 154 is compressed between a top 140a of the communications module 140 and the internal wall 150a of the parachute module 150. The spring 154 in this example is a conical spring, but other forms of springs may be used. In addition, one should appreciate that the spring 154 may be optional in some embodiments, as mild agitation by waves, wind, and/or currents may be sufficient to separate the two modules without requiring a spring. Also, the spring 154 may be implemented as a magnetic, hydraulic, or pneumatic spring, rather than as a mechanical spring as shown.

In the illustrated arrangement, it is only the retaining structure 220 that prevents the modules 140 and 150 from separating. For example, if the retaining structure 220 were absent, the head of the fastener 210 would pull out of the communications module 140 and the parachute module 150 would float away.

Effectively this action takes place when the device 102 lands in water. Passageways 420 and 422 allow liquid water to enter the top of the communications module 140 and reach the retaining component 220, bathing the bobbin pill 220d in water and causing it to lose its initial rigidity, e.g., by dissolving. When the bobbin pill 220d softens, the internal fingers 220b splay open, e.g., due to the force of the spring 154 driving the tapered head 210h of the fastener 210 through the opening at the top of the module 140. As the retaining component 220 can no longer prevent the modules 140 and 150 from separating, the repulsive force of the spring 154 pushes up on the parachute module 150, pulling the head 210h of the fastener 210 completely out of the communications module 140 and freeing the parachute module 150 from the communications module 140.

One should appreciate that the passageways 420 and 422 normally prevent water from entering the module 140 unless the device 102 is at least partially submerged in water. For example, with the device 102 oriented vertically, as is the case when the device 102 is carried by the parachute 152, the passageways 422 are angled down so as to prevent raindrops or runoff from rain from entering the module 140. Rather, it is only when the device 102 is submerged above the level of the passageways 422 that water may enter the module 140. In some examples, passageways 420 and 422 include baffling to further prevent water entry unless the module 140 is submerged. Such baffling may take the form of partial walls and/or circuitous routes that restrict sloshing and ensure that the retaining structure 220 is exposed to liquid water only in the event of at least partial submergence. Some examples do not require such baffling, however.

Figure 5A:
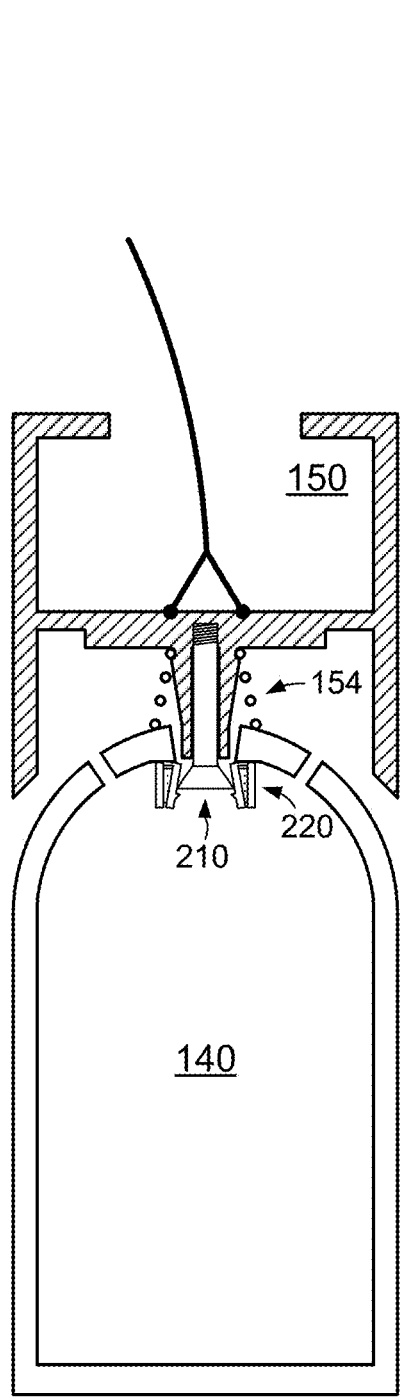
FIGS. 5A and 5B are cross-sectional views that show the parachute module and communications module of FIG. 4 becoming detached.
Figure 5B:
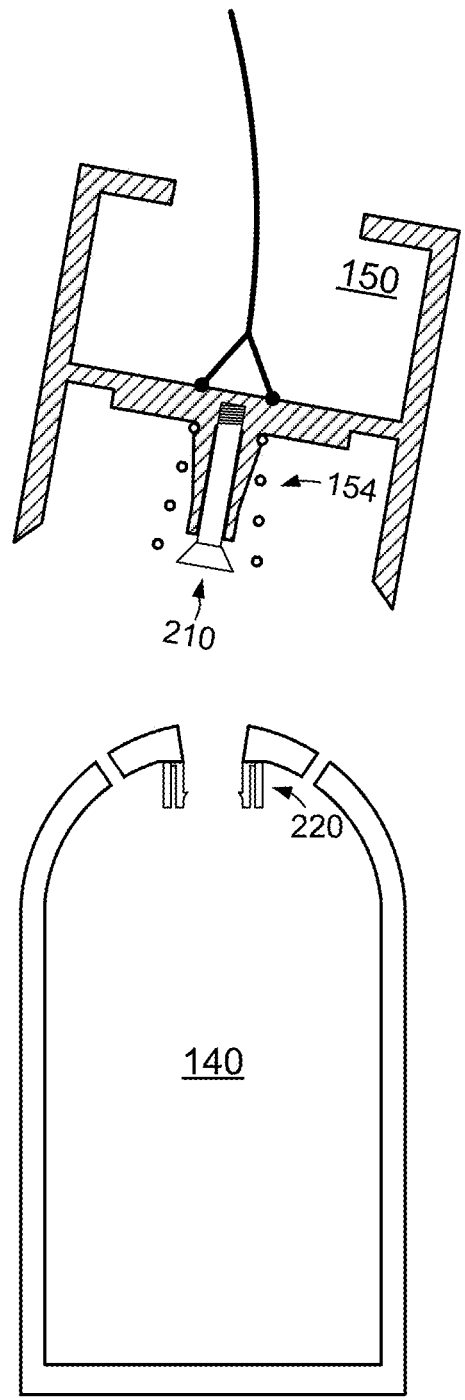

FIGS. 5A and 5B show various levels of separation. In FIG. 5A, the head 210h of the fastener 210 has partially pulled through the retaining component 220, with the internal fingers 220b splaying open. Spokes 220c are easily compressed or pushed aside. As shown in FIG. 5B, the two modules 140 and 150 have completely separated. Spring 154 is fully extended.

Figure 6A:
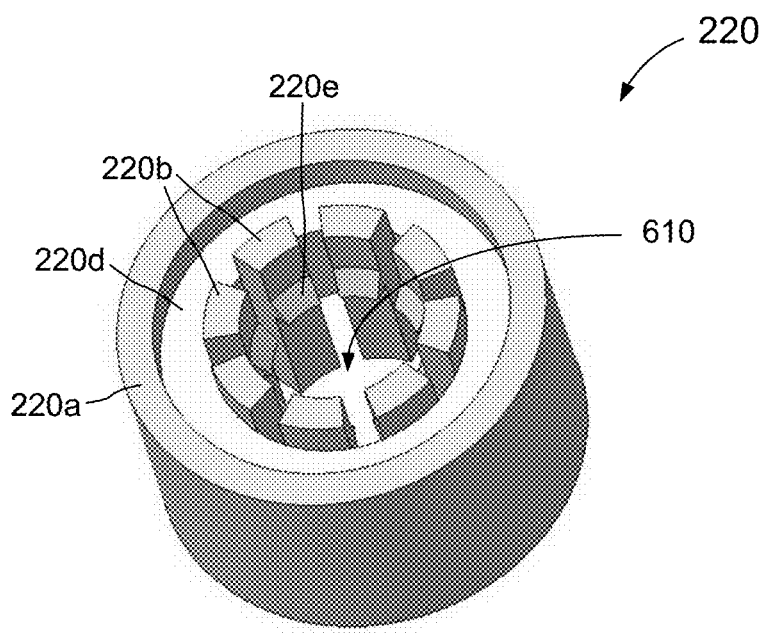
FIGS. 6A and 6B are perspective and top plan views, respectively, of an example retaining component used in the attachment of FIGS. 4, 5A, and 5B.
Figure 6B:
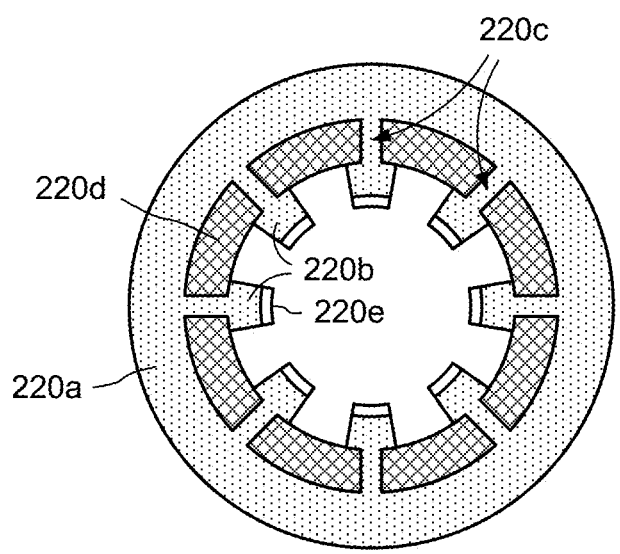

FIGS. 6A and 6B show example features of the retaining structure 220 in additional detail. FIG. 6A is a bottom view and shows the outer wall 220a, which extends completely around and contains the bobbin pill 220d, and internal fingers 220b (8 fingers shown in the figure), which support the bobbin pill 220d internally. The internal fingers 220b also provide an abutment for the head of fastener 210. Each finger 220b has a respective step 220e. The retaining structure 220 is seen to have an annular shape and a central hole 610 through which the fastener 210 may pass.

FIG. 6A is a top view of the retaining structure 220 and further shows spokes 220c, e.g., one spoke 220c for each finger 220b. The spokes 220c are flexible and easily deformed.

Figure 7:
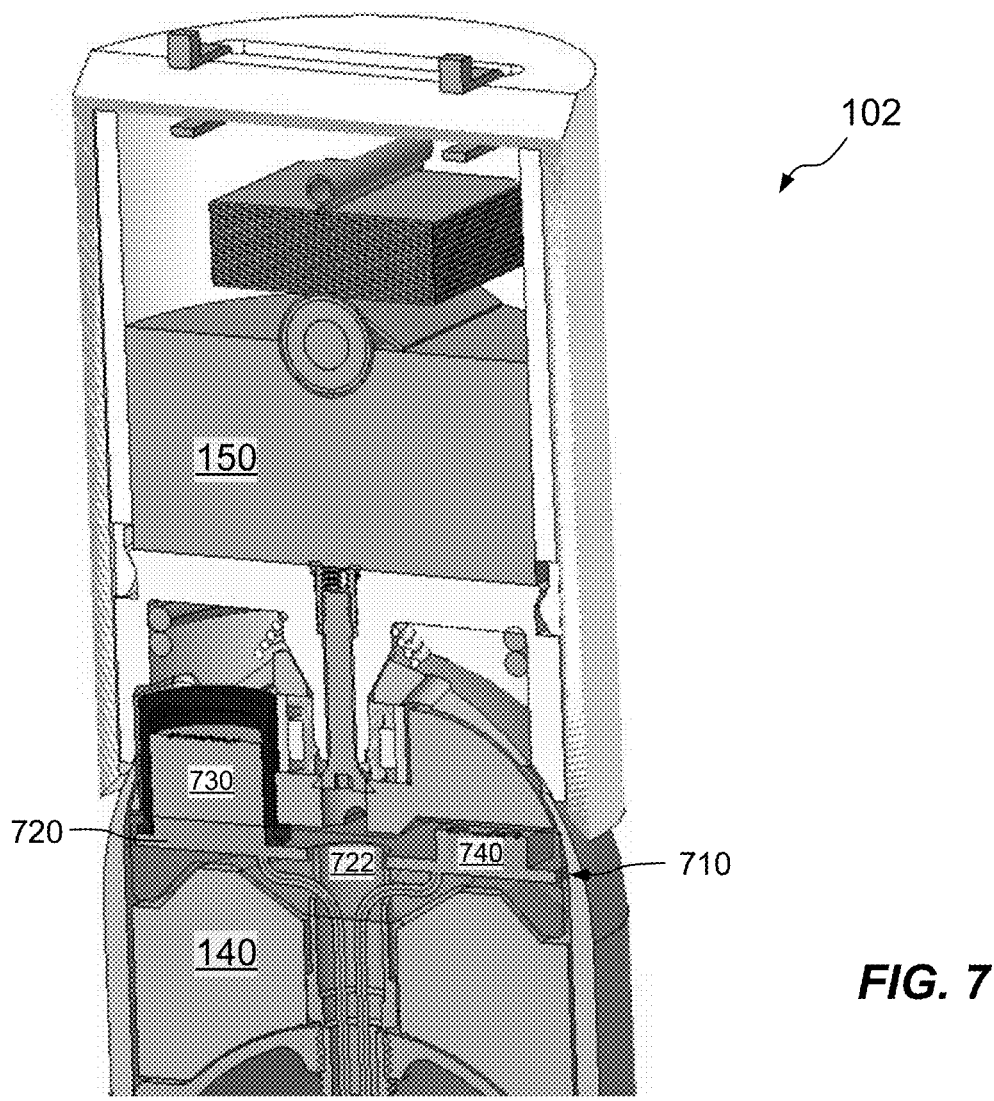
FIG. 7 is a perspective sectional view showing an example parachute module, communications module, and attachment.

FIG. 7 is a perspective sectional view of an example device 102, showing an example communications module 140, parachute module 150, and attachment therebetween. In this example, the communications module 140 includes an antenna assembly 710, which includes a substrate 720 (e.g., a circuit board or other carrier), a satellite communications antenna 730 and a GPS (Global Positioning Service) antenna 740). As shown by non-limiting example, the substrate 720 of the antenna assembly 710 may be disk-shaped and may include a central hole 722. Certain details of the modules 140 and 150 may differ slightly from those shown in previous figures, underscoring the diversity of embodiments that are contemplated.

Figures 8A, 8B:
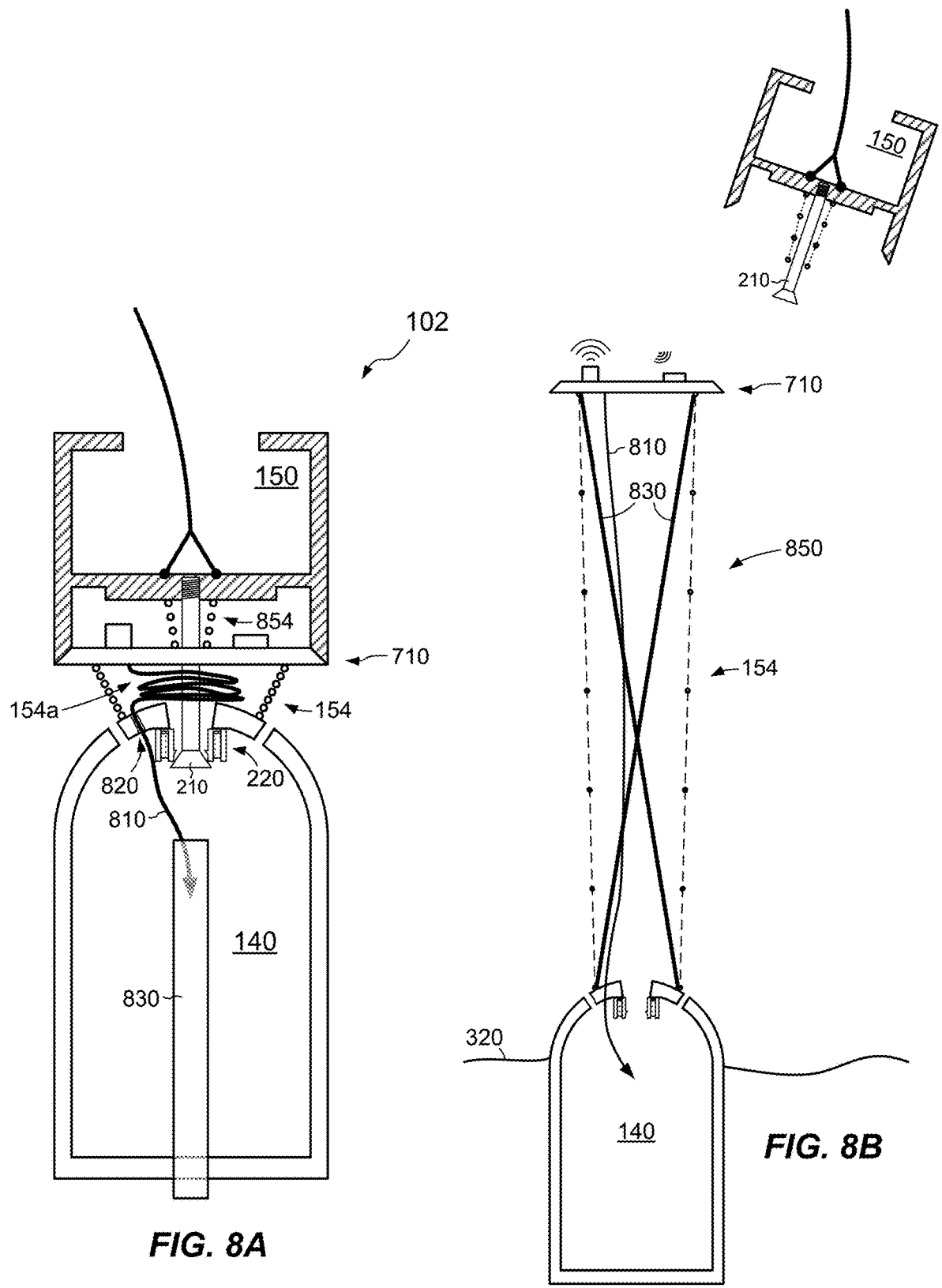
FIGS. 8A and 8B are cross-sectional views that show an example antenna assembly initially disposed between a parachute module and a communications module (FIG. 8A) and later deployed on a mast (FIG. 8B).

FIGS. 8A and 8B show yet another embodiment, which may provide for improved signal communications via the antenna assembly 710. As shown in FIG. 8A, the antenna assembly 710 is positioned outside the communications module 140, sandwiched between the two modules 140 and 150. Cabling 810 (i.e., one or more cables) convey signals from antenna assembly 710 into the communications module 140, e.g., via a waterproof penetrator 820, such as a potted bore or a submersible connector. The cabling 810 may further extend into the electronics module 130, e.g., via a tube 830. In an example, the cabling 810 is packed inside the spring 154. For example, the spring 154 has a central region 154a that can accommodate cabling 810. The cabling 810 is long enough to reach the parachute module 150 when the spring 154 is fully extended. A somewhat longer version of spring 154 may be provided for this embodiment as compared with the embodiments described above, to support longer extension and to enable the spring 154 to server as a mast 850. Also, the spring 154 in this example may have a fixed attachment both to the top of the parachute module 150 and to the antenna assembly 710.

Optionally, a second spring 854, such as another conical spring, may be placed between the antenna assembly 710 and the parachute assembly 150, to ensure complete separation of the parachute module 150 from the electronics assembly 710 when the parachute module 150 disconnects. The second spring 854 may not be required in certain embodiments, however.

Disconnection of the parachute module 150 proceeds much as described above. For example, the device 102 lands in water. Water enters the communications module 140 and reaches the retaining component 220. The retaining component 220 transitions upon exposure to liquid water from a first state in which the retaining component 220 is rigid to a second state in which the retaining component loses its rigidity and becomes compliant. Once the retaining component 220 transitions from the first state to the second state, the retaining component 220 can no longer hold back the head of fastener 210. Under the influence of spring 154, the head of the fastener pulls through the retaining component 220 and out the top of the communications module 140.

FIG. 8B shows an example result of separation. After pulling through the top of the communications module 140, the fastener 210 pulls through the antenna assembly 710 (FIG. 7) and is carried away with the parachute module 150, which fully disconnects from the device 102. The spring 154 has fully released and forms a mast 850 that extends from the communications module 140 to the antenna assembly 710. The mast 850 has sufficient length so that it extends above the surface 320 of the water, thus facilitating wireless communications. In some examples, tendons 830 may be provided to reduce lateral flexing of the mast 850. For example, multiple tendons 830 are disposed within the spring 154 and are arranged to cross. Each of the tendons 830 attaches to the communications module 140 at one end and to the antenna assembly 710 at the other end. The tendons 830 may be composed of an easily-compactable material that resists stretching, such as fabric or string.

Figure 9A:
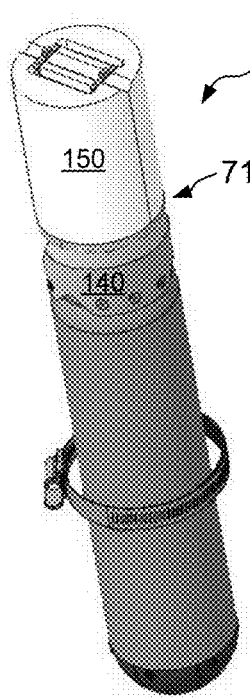
FIGS. 9A-9C are perspective views of another embodiment in which an example antenna assembly is initially disposed between a parachute module and a communications module.
Figure 9B:
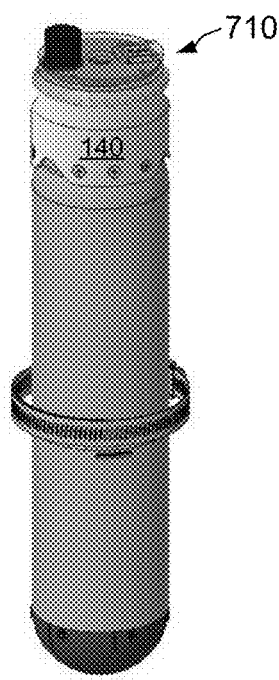
Figure 9C:
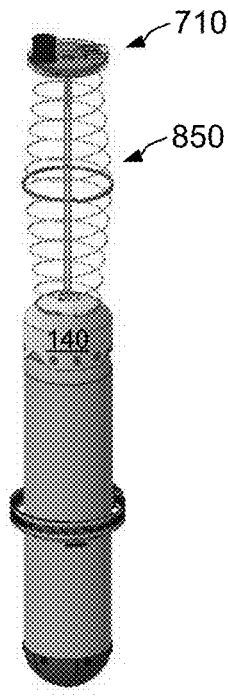

FIGS. 9A-9C show a variant of the embodiment of FIGS. 8A and 8B. FIG. 9A shows the device 102 prior to separation of module 150 from module 140, with the antenna assembly 710 placed between the two modules. FIG. 9B shows the device 102 with the parachute module hidden but not separated, revealing more fully the antenna assembly 710. FIG. 9C shows the device 102 after the spring 154 has extended to form mast 850 and the parachute module 150 has been jettisoned.

Figure 10:
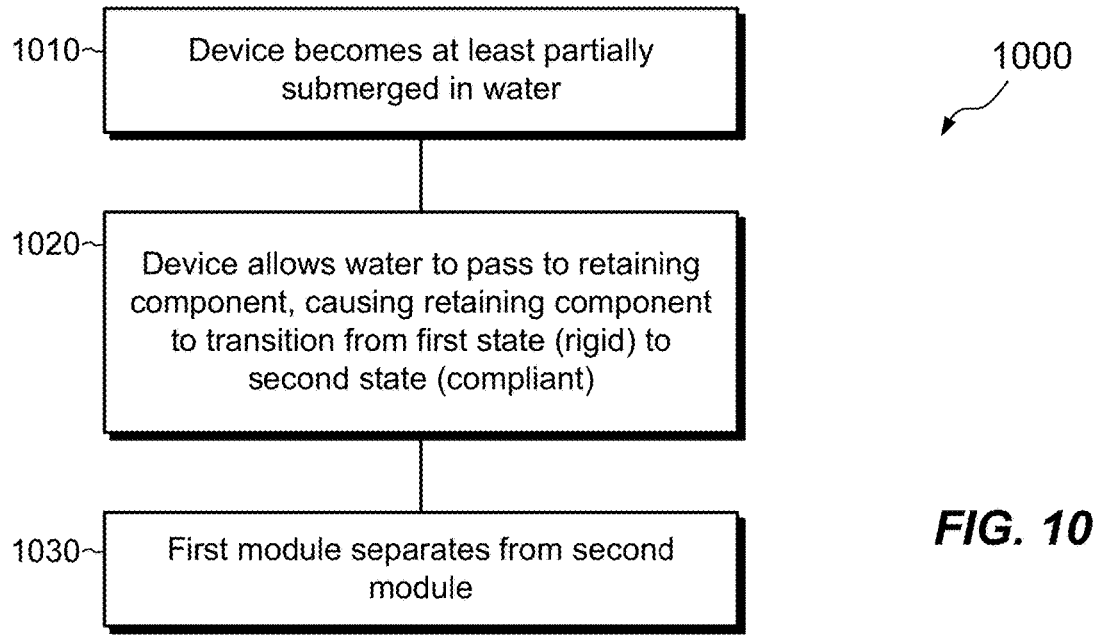
FIG. 10 is a flowchart showing an example method of managing an attachment between first and second portions of a device.

FIG. 10 shows an example method 1000 of managing an attachment between different portions of a device 102 and provides a summary of certain features described above. At 1010, the device 102 becomes at least partially submerged in water, as shown in FIG. 3. For example, the device 102 may be a dropsonde deployed from an aircraft. At 1020, the device 102 allows water to enter the module 140, e.g., via passageways 420 and 422, and to pass to the retaining component 220. Upon exposure to liquid water, the retaining component 220 transitions from the first state, in which the retaining component has a rigid characteristic, to the second state, in which the retaining component loses its rigid characteristic and becomes compliant, e.g., by virtue of the bobbin pill 220d becoming wet and softening or dissolving. At 1030, upon the transition from the first state to the second state, the parachute module 150 separates from the communications module 140, e.g., as a result of the fastener 210 pulling through the retaining component 220 under an imposed force from the spring 154. The device 102 is then free from the parachute module 150 and is able to descend within the water and to make measurements.

An improved technique has been described for managing an attachment between first and second portions of a device 102. The technique includes a retaining component 220 having a first state in which the retaining component 220 maintains the attachment by virtue of a rigid characteristic and a second state in which the retaining component 220 loses the rigid characteristic and no longer maintains the attachment. The retaining component 220 transitions from the first state to the second state upon exposure to liquid water. Advantageously, the improved technique requires no power, sensor, or control circuitry and operates reliably in salt-water environments.

Having described certain embodiments, numerous alternative embodiments or variations can be made. For example, although embodiments have been described in which the device 102 is a dropsonde, this is merely an example, as the device 102 may alternatively be a sonde, a buoy, or any device that may be used in an aqueous environment. Further, the depicted separation of a parachute module 150 from a communication module 140 is also merely an example. Thus, separation may be managed between any modules or other portions of the device 102. The portions need not qualify as modules, per se, and the device 102 need not itself be a modular device. For instance, embodiments may involve disconnecting ballast or payload from the device 102, or dropping a sensor from a larger module or device.

Although the retaining component 220 has been shown and described as having an annular shape, it may alternatively have different shapes. Further, it is not required that a fastener pull through the retaining component 220. Rather, the retaining component 220 may be any element having any shape that prevents separation of two portions when dry but allows separation when wet.

Further, although features have been shown and described with reference to particular embodiments hereof, such features may be included and hereby are included in any of the disclosed embodiments and their variants. Thus, it is understood that features disclosed in connection with any embodiment are included in any other embodiment.

As used throughout this document, the words "comprising," "including," "containing," and "having" are intended to set forth certain items, steps, elements, or aspects of something in an open-ended fashion. Also, as used herein and unless a specific statement is made to the contrary, the word "set" means one or more of something. This is the case regardless of whether the phrase "set of" is followed by a singular or plural object and regardless of whether it is conjugated with a singular or plural verb. Also, a "set of" elements can describe fewer than all elements present. Thus, there may be additional elements of the same kind that are not part of the set. Further, ordinal expressions, such as "first," "second," "third," and so on, may be used as adjectives herein for identification purposes. Unless specifically indicated, these ordinal expressions are not intended to imply any ordering or sequence. Thus, for example, a "second" event may take place before or after a "first event," or even if no first event ever occurs. In addition, an identification herein of a particular element, feature, or act as being a "first" such element, feature, or act should not be construed as requiring that there must also be a "second" or other such element, feature or act. Rather, the "first" item may be the only one. Also, and unless specifically stated to the contrary, "based on" is intended to be nonexclusive. Thus, "based on" should not be interpreted as meaning "based exclusively on" but rather "based at least in part on" unless specifically indicated otherwise. Although certain embodiments are disclosed herein, it is understood that these are provided by way of example only and should not be construed as limiting.

Those skilled in the art will therefore understand that various changes in form and detail may be made to the embodiments disclosed herein without departing from the scope of the following claims.

What is claimed is:

1. An apparatus, comprising:
a first portion;
a second portion;
a retaining component, the retaining component having a first state and a second state, the retaining component configured to (i) in the first state, have a rigid characteristic and hold the first portion together with the second portion, (ii) transition from the first state to the second state in response to submersion in water, and (iii) in the second state, lose its rigid characteristic and free the first portion from the second portion, wherein the retaining component in the first state is disposed within one of the first portion and the second portion;
a set of passageways that allows water to reach the retaining component;
a spring disposed between the first portion and the second portion, the spring configured to push the first portion away from the second portion in response to the retaining component transitioning from the first state to the second state; and
an antenna assembly disposed between the first portion and the second portion with the retaining component in the first state, the antenna assembly including a set of antennas,
wherein the spring has a first end coupled to the antenna assembly and a second end coupled to the second portion, and wherein the antenna assembly is configured to extend away from the second portion but remain attached thereto via the spring in response to the retaining component transitioning from the first state to the second state.

2. The apparatus of claim 1, wherein the retaining component in the first stat has a hole therethrough, and wherein the apparatus further comprises a fastener having a head and a shaft, the head abutting the retaining component and the shaft extending through the hole and into the other of the first portion and the second portion, where the shaft is retained therein.

3. The apparatus of claim 2, wherein head of the fastener is configured to pull through the hole in the retaining component in response to the retaining component transitioning from the first state to the second state.

4. The apparatus of claim 3, wherein the retaining component in the first state is disposed within the second portion, and wherein the set of passageways is configured to conduct water to the retaining component in the second portion.

5. The apparatus of claim 4, wherein the apparatus has a vertical orientation, and wherein the passageways are angled downwardly with the apparatus in the vertical orientation to prevent rain water from entering through the passageways while the apparatus falls through air.

6. The apparatus of claim 1, wherein the first portion is a parachute module configured to deploy a parachute coupled to the parachute module, and wherein the retaining component is operative to release the parachute module from the second portion in response to the apparatus landing in water.

7. The apparatus of claim 1, further comprising ballast configured to keep the apparatus vertical in water, and wherein the antenna assembly is configured to extend out of the water with the spring extended.

8. The apparatus of claim 1, wherein the spring has a central region, and wherein the apparatus further comprises cabling that extends from the antenna assembly, through the central region of the spring, and into the second portion.

9. The apparatus of claim 8, further comprising a set of tendons that pass through the central region of the spring, each of the set of tendons connecting to the antenna assembly at one end and to the second portion at another end, the set of tendons configured to reduce lateral flexing of the spring when the spring is extended.

10. The apparatus of claim 8, further comprising a fastener having a head and a shaft, the shaft passing between the first portion and the second portion and through a hole in the antenna assembly.

11. The apparatus of claim 10, further comprising a second spring disposed between the first portion and the antenna assembly, the second spring configured to push the first portion away from the antenna assembly in response to the retaining component transitioning from the first state to the second state.

12. A method of managing an attachment between a first portion and a second portion of a device, the method comprising:
providing a retaining component having a first state and a second state, the retaining component configured to (i) in the first state, have a rigid characteristic and hold the first portion together with the second portion, (ii) transition from the first state to the second state in response to submersion in water, and (iii) in the second state, lose its rigid characteristic, wherein the retaining component in the first state is disposed within one of the first portion and the second portion, and wherein the device includes a set of passageways that allows water to reach the retaining component;
with the retaining component in the first state, the device becoming at least partially submerged in water;
the device allowing water to pass to the retaining component, the retaining component thereupon transitioning from the first state to the second state and freeing the first portion from the second portion;
actively pushing the first portion away from the second portion in response to the retaining component transitioning from the first state to the second state; and
providing an antenna assembly, wherein actively pushing the first portion away from the second portion includes pushing the antenna assembly out of the water.

13. The method of claim 12, wherein the retaining component retains the first portion to the second portion by preventing a fastener from pulling through a hole in the retaining component, and wherein the method further comprises the fastener pulling through the hole in the retaining component in response to the retaining component transitioning from the first state to the second state.

14. The method of claim 12, wherein transitioning from the first state to the second state includes the retaining component or a portion thereof dissolving in water.

15. The method of claim 12, further comprising preventing liquid water from contacting the retaining component until the device is at least partially submerged in the water.

16. The method of claim 12, wherein the first portion is a parachute module, and wherein the retaining component releases the parachute module from the second portion in response to the apparatus becoming at least partially submerged in the water.

17. An apparatus, comprising:
a first portion;
a second portion;
a retaining component, the retaining component having a first state and a second state, the retaining component configured to (i) in the first state, have a rigid characteristic and hold the first portion together with the second portion, (ii) transition from the first state to the second state in response to submersion in water, and (iii) in the second state, lose its rigid characteristic and free the first portion from the second portion, wherein the retaining component in the first state is disposed within one of the first portion and the second portion;
a set of passageways that allows water to reach the retaining component; and
a set of antennas coupled to a spring disposed between the first portion and the second portion, the spring configured to push the first portion away from the second portion and to push the set of antennas out of the water in response to the retaining component transitioning from the first state to the second state.

18. The apparatus of claim 17, wherein the spring has a first end coupled to the set of antennas and a second end coupled to the second portion, and wherein the set of antennas is configured to extend away from the second portion but remain attached thereto via the spring in response to the retaining component transitioning from the first state to the second state.

19. The apparatus of claim 17, further comprising ballast configured to keep the apparatus vertical in the water when the spring is extended.

\* \* \* \* \*